US011278197B1

(12) United States Patent
Bajunaid et al.

(10) Patent No.: US 11,278,197 B1
(45) Date of Patent: Mar. 22, 2022

(54) COMBINATION CHEEK RETRACTOR/MOUTH MIRROR ATTACHMENT FOR DENTAL TOOL

(71) Applicant: KING SAUD UNIVERSITY, Riyadh (SA)

(72) Inventors: Salwa Omar Bajunaid, Riyadh (SA); Bader Khaled Albalkhi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/907,146

(22) Filed: Jun. 19, 2020

(51) Int. Cl.
*A61B 1/247* (2006.01)
*A61B 1/32* (2006.01)
*A61B 1/00* (2006.01)

(52) U.S. Cl.
CPC ............ *A61B 1/247* (2013.01); *A61B 1/0014* (2013.01); *A61B 1/32* (2013.01)

(58) Field of Classification Search
CPC ......... A61B 1/247; A61B 1/0014; A61B 1/32; A61B 1/24; A61B 1/00131
USPC ........................................................ 433/141
See application file for complete search history.

(56) References Cited

U.S. PATENT DOCUMENTS

| 1,054,488 | A | * | 2/1913 | Mailey | A61B 1/247 |
| | | | | | 433/31 |
| 1,844,733 | A | | 2/1932 | Wise | |
| 2,582,121 | A | | 1/1952 | Harvey | |
| 4,219,331 | A | | 8/1980 | Getz | |
| 4,465,461 | A | | 8/1984 | Schutz | |
| 4,790,751 | A | | 12/1988 | Reinhardt et al. | |
| 5,882,195 | A | * | 3/1999 | Low | A61B 1/247 |
| | | | | | 433/140 |
| 6,666,682 | B1 | * | 12/2003 | Meyerhof | A61B 1/24 |
| | | | | | 433/31 |
| 7,021,780 | B2 | * | 4/2006 | Kasem | A61B 1/247 |
| | | | | | 359/881 |
| 9,585,549 | B1 | * | 3/2017 | Elazar | A61B 5/067 |

(Continued)

FOREIGN PATENT DOCUMENTS

CN 209529084 U 10/2019

OTHER PUBLICATIONS

"Moth Mirror | Cheek Retractoe| Magnifying", Laramie Medical Solutions Co. (2019), published at laramiems.co.uk/product/mouth-mirror-cheek-retractor/, 3 pages.

*Primary Examiner* — Nicholas D Lucchesi
*Assistant Examiner* — Mirayda A Aponte
(74) *Attorney, Agent, or Firm* — Nath, Goldberg & Meyer; Richard C. Litman

(57) ABSTRACT

The combination cheek retractor/mouth mirror attachment for a dental tool is a single unit that has three main portions. The attachment includes a main body portion (cheek retractor), a mirror portion, and a connector portion for attaching a dental tool, such as a probe or dental explorer. The main body portion is an arcuate body defining a border or frame having parallel arcuate upper and lower arms, the ends of the arms being joined by short, parallel legs, the corners being rounded. The mirror portion is an arcuate, single-face plane mirror fixed within the frame of the cheek retractor by gluing, welding, or the like. The connector portion is a split ring annular collar or band extending from the cheek retractor and having parallel tabs with aligned holes receiving a fastener for clamping the attachment to the neck of a dental tool, such as an explorer or probe.

4 Claims, 5 Drawing Sheets

(56) References Cited

U.S. PATENT DOCUMENTS

| | | |
|---|---|---|
| 9,610,009 B2 | 4/2017 | Motamedi |
| 2005/0277085 A1 | 12/2005 | Coleton |
| 2013/0252197 A1 | 9/2013 | Harden |
| 2017/0089382 A1* | 3/2017 | VerBrugge ............ F16B 21/186 |
| 2017/0280987 A1 | 10/2017 | Weiandt |

* cited by examiner

COMBINATION CHEEK RETRACTOR/MOUTH MIRROR ATTACHMENT FOR DENTAL TOOL

1. FIELD

The disclosure of the present patent application relates to dental tools, and particularly to a combination cheek retractor/mouth mirror attachment for a dental tool, such as a dental explorer, periodontal probe, or the like.

2. DESCRIPTION OF THE RELATED ART

Several types of cheek retractors are currently used by dental health professionals, dental hygienists, and dental assistants in the field of dentistry. Generally, a dental patient would be treated by a two-person team that comprises a dental professional and a dental assistant. Further, dental treatment may be provided by the team using many different types of dental equipment and materials. Such dental equipment and materials may include items such as a mouth mirror, a dental explorer, a cheek retractor, a dental probe, etc. Each element of dental equipment may be used for different purposes, though some may be used in combination for some types of dental services. In general, a dentist seeking to provide such dental services may need to use multiple items of such dental equipment. An important role of the dental assistant is therefore to assist the dental professional in coordinating the use of these multiple items of different equipment.

During the routine dental check-up, such as while checking the marginal gap between an artificial dental crown and the natural tooth using an explorer, or checking the periodontal pocket depth between the gingiva and the tooth using a periodontal probe inside the patient's mouth, maximum retraction of the cheek is necessary to allow access to soft and hard tissues. Moreover, all the time a mouth mirror is used by dentists to have a view of mouth portions that are not easy to access directly. So, conventionally, in one hand the dental professional holds a mouth mirror and in other hand a dental explorer, and therefore cheek retractors are fitted to the patient's mouth externally, which causes pain and discomfort.

Therefore, there is a need in the art for improved systems and methods of providing dental services in a more efficient, comfortable, and safe manner to the dental patient. There is also a need for instruments that are comfortable for dental professionals. However, most designs for cheek retractors concentrates on integrating cheek retraction with lip retraction, or their devices are to be fitted to patient's mouth, which causes inconvenience and discomfort to patients. Thus, a combination cheek retractor/mouth mirror attachment for a dental tool solving the aforementioned problems is desired.

SUMMARY

The combination cheek retractor/mouth mirror attachment for a dental tool is a single unit that has three main portions. The attachment includes a main body portion (cheek retractor), a mirror portion, and a connector portion for attaching a dental tool, such as a probe or dental explorer. The main body portion is an arcuate body defining a border or frame having parallel arcuate upper and lower arms, the ends of the arms being joined by short, parallel legs, the corners being rounded. The mirror portion is an arcuate, single-face plane mirror fixed within the frame of the cheek retractor by gluing, welding, or the like. The connector portion is a split ring annular collar or band extending from the cheek retractor and having parallel tabs with aligned holes receiving a fastener for clamping the attachment to the neck of a dental tool, such as an explorer or probe.

The main body portion may be made of a stainless steel or cobalt chromium. The angle of the cheek retractor portion is set to a value that results in efficient check retraction without any discomfort to patient. The connector portion may be provided in different sizes or diameters so that it can accommodate dental explorers or dental probes of different diameters.

The combination cheek retractor/mouth mirror attachment for a dental tool provides a cheek retractor that permits the cheeks to spread in such a manner as to ensure free access to the areas to be treated, and which is so designed so that even a prolonged application of the retractor is not uncomfortable or even painful for the patient, as well as dental professional. It is designed in such a way that it is capable of being used on either side of the mouth. The attachment provides a cheek retractor usable as a one-handed device integrated with a dental explorer or probe and a mouth mirror.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The combination cheek retractor/mouth mirror attachment for a dental tool is a single unit that has three main portions. The attachment includes a main body portion (cheek retractor), a mirror portion, and a connector portion for attaching a dental tool, such as a probe or dental explorer. The main body portion is an arcuate body defining a border or frame having parallel arcuate upper and lower arms, the ends of the arms being joined by short, parallel legs, the corners being rounded. The mirror portion is an arcuate, single-face plane mirror fixed within the frame of the cheek retractor by gluing, welding, or the like. The connector portion is a split ring annular collar or band extending from the cheek retractor and having parallel tabs with aligned holes receiving a fastener for clamping the attachment to the neck of a dental tool, such as an explorer or probe.

Figure 1:
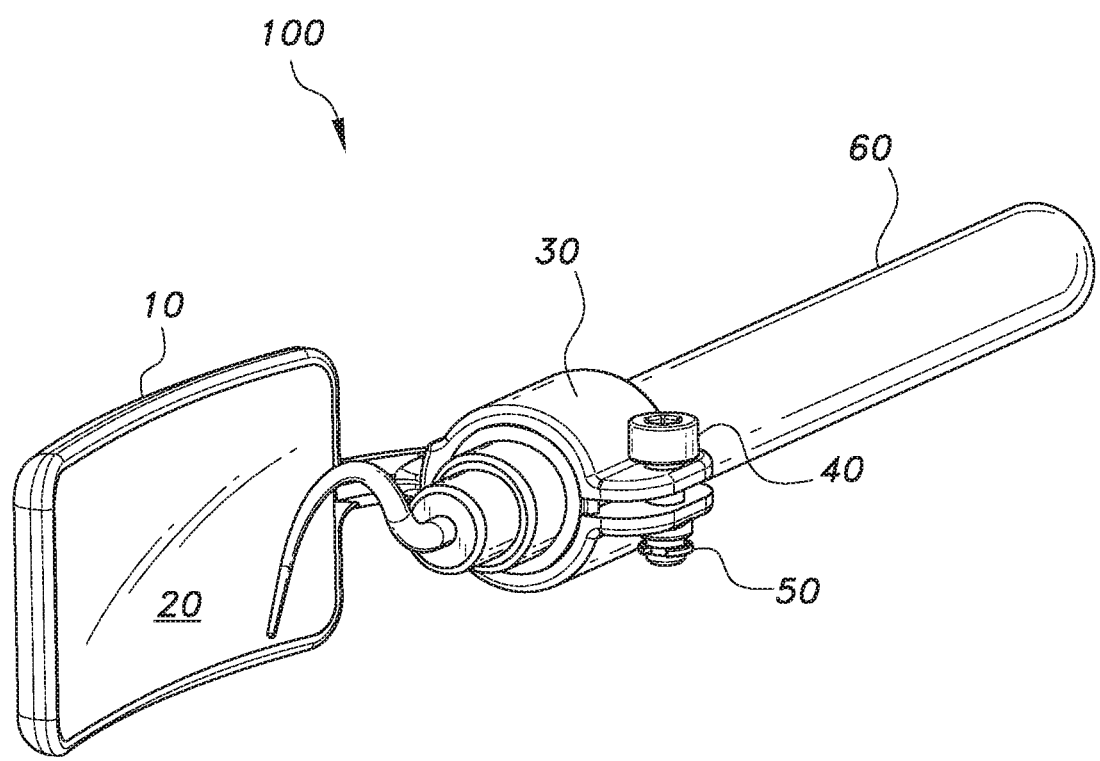
FIG. 1 is an environmental, perspective view of a combination cheek retractor/mouth mirror attachment for a dental tool.
Figure 2:
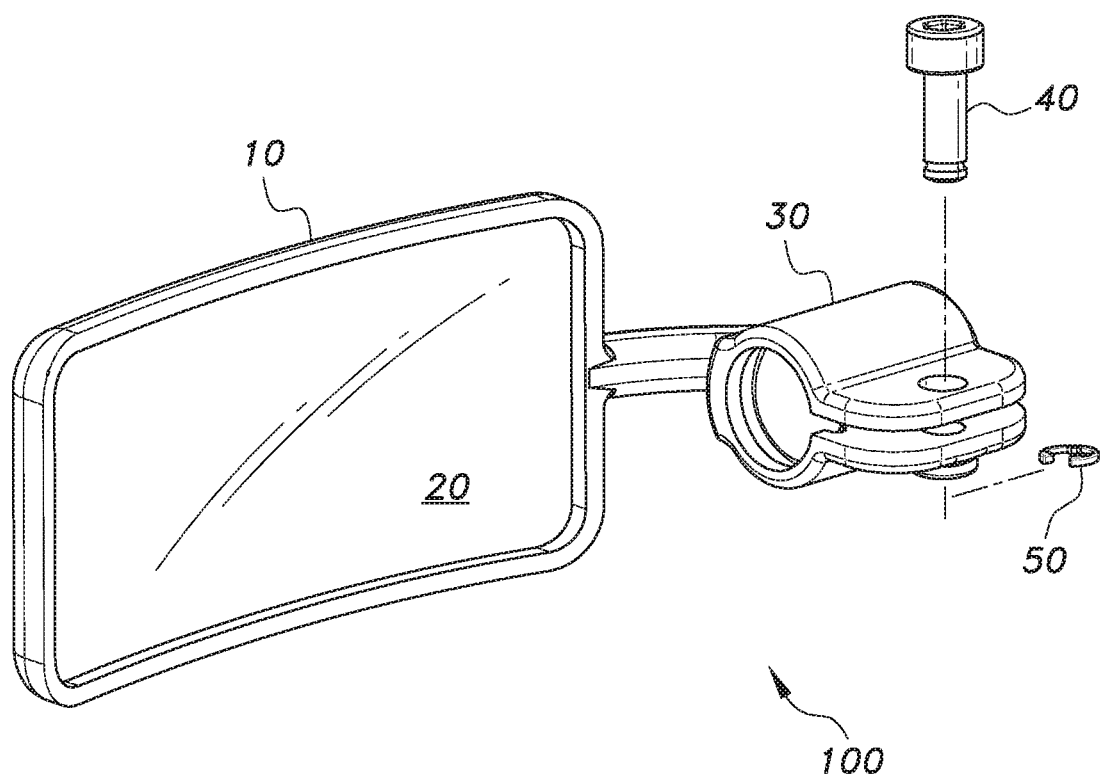
FIG. 2 is a partially exploded perspective view of the combination cheek retractor/mouth mirror attachment of FIG. 1.

FIGS. 1 and 2 show a combination cheek retractor/mouth mirror attachment for a dental tool, the attachment being designated generally as 100 in the drawings. FIG. 1 shows the attachment 100 in use with a dental explorer 60, and FIG. 2 shows the attachment 100 by itself, without a dental tool. The attachment 100 includes a cheek retractor 10 having an arcuate body and a mouth mirror 20 attached to the cheek retractor 10. The attachment 100 also includes a connector collar 30, which is a split ring collar connected to the cheek retractor 10 by a cylindrical connector arm 25. A fastener, such as a cap screw or pin 40 and a snap ring 50, are used to clamp the attachment 100 to the neck of the dental tool 60, so that the elongate handle of the explorer 60 serves also as a handle for the cheek retractor 10 and the mouth mirror 20.

The cheek retractor 10 is of curved rectangular shape. The curvature angle of the arm attaching the cheek retractor 10 to the collar 30 is kept at 40° with respect to the plane of the top edge of the collar 30. The curvature angle will give the ease and comfort for both dentist and patient. The retractor 10 is preferably made of one solid piece of surgical grade steel. The cheek retractor 10 and mouth mirror 20 form one solid piece, which is connected to the dental explorer or probe 60 through the collar 30. The collar 30 is an annular band or collar used to clamp the attachment around the neck of the dental tool between the elongate handle and hook of the dental tool (shown as a dental explorer, which is also known as a sickle probe, in FIG. 1). In one embodiment, the collar 30 has an inside diameter (I.D.) of 10 mm and an outside diameter (O.D.) of 12.5 mm. In another embodiment, the collar 30 has an I.D. of 6.5 mm and an O.D. of 8.5 mm. The different dimensions are designed to accommodate explorers and probes of different diameter.

Figure 3:
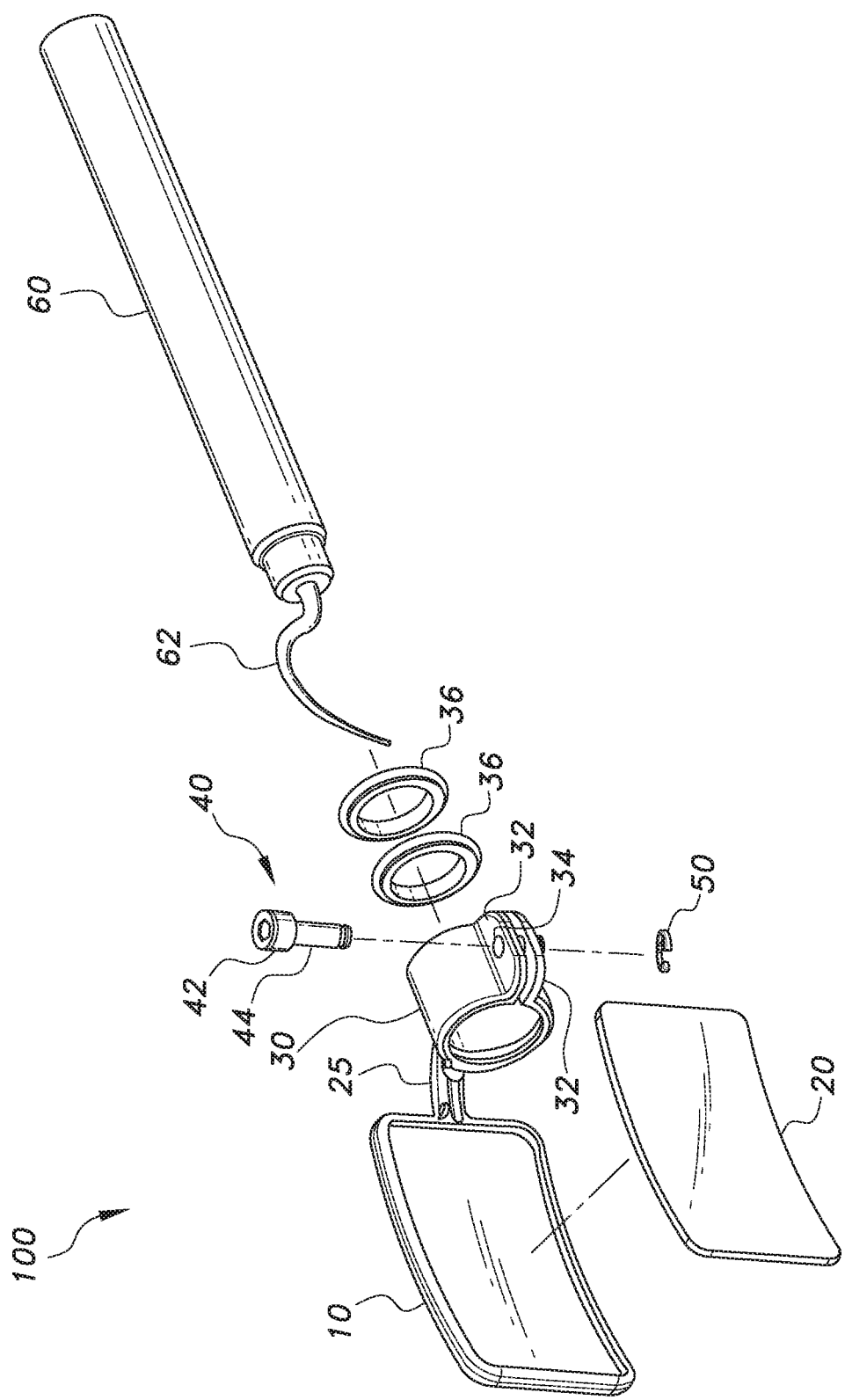
FIG. 3 is an exploded perspective view of the combination cheek retractor/mouth mirror attachment of FIG. 1.

FIG. 3 is an exploded view showing the components of the attachment 100 in greater detail. The cheek retractor 10 has a border or frame defined by parallel upper and lower arcuate arms joined by short vertical legs forming a rectangular frame. The cheek retractor 10 may have rounded corners to protect the buccal, gingival, and other sensitive tissue inside the patient's mouth while retracting the cheek and examining the tissue. The mouth mirror 20 is an arcuate plane mirror having the same arcuate shape as the cheek retractor 10 and is fixed within the frame by adhesive or welding to form one piece. The connector or collar 30 is attached to the cheek retractor 10 by a cylindrical connector arm 25. The collar is split on the side diametrically opposite the arm 25 and has two parallel tabs 32 extending normal to the cylindrical body. The tabs 32 have aligned holes 34 defined there. The shank 44 of a cap screw or pin 40 having a hex socket head 42 is inserted through the aligned holes 32 and secured by a snap ring 50 to clamp the collar 30 to the explorer 60 or other dental tool. The explorer 60 has a hook or sickle-shaped probe 62. A pair of rubber or silicone rings 36 may be mounted inside the collar 30 at opposite ends thereof to protect the finish of the explorer 60.

Figure 4:
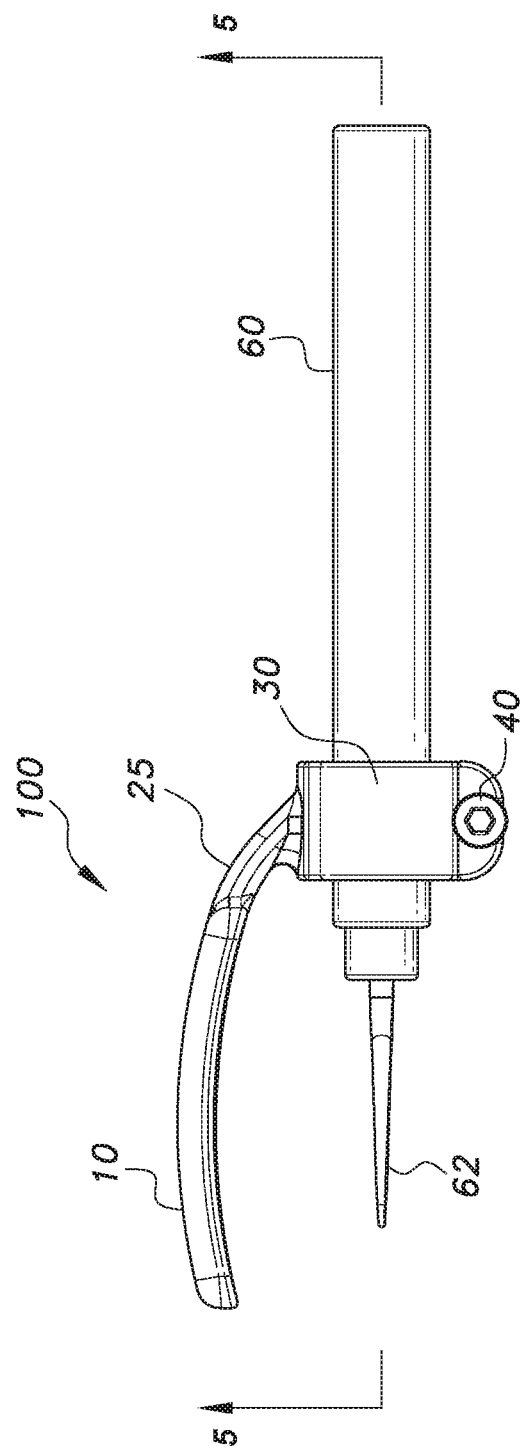
FIG. 4 is an environmental top view of the combination cheek retractor/mouth mirror attachment of FIG. 1.
Figure 5:
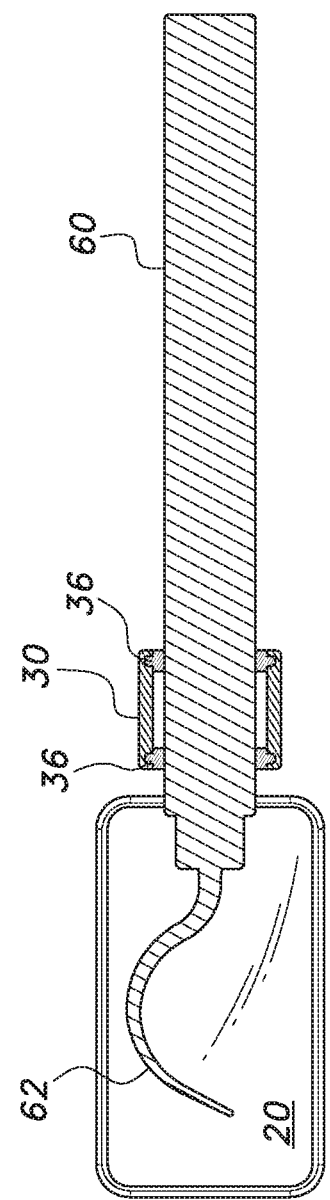
FIG. 5 is a section view drawn along lines 5-5 of FIG. 4.
Figure 6:
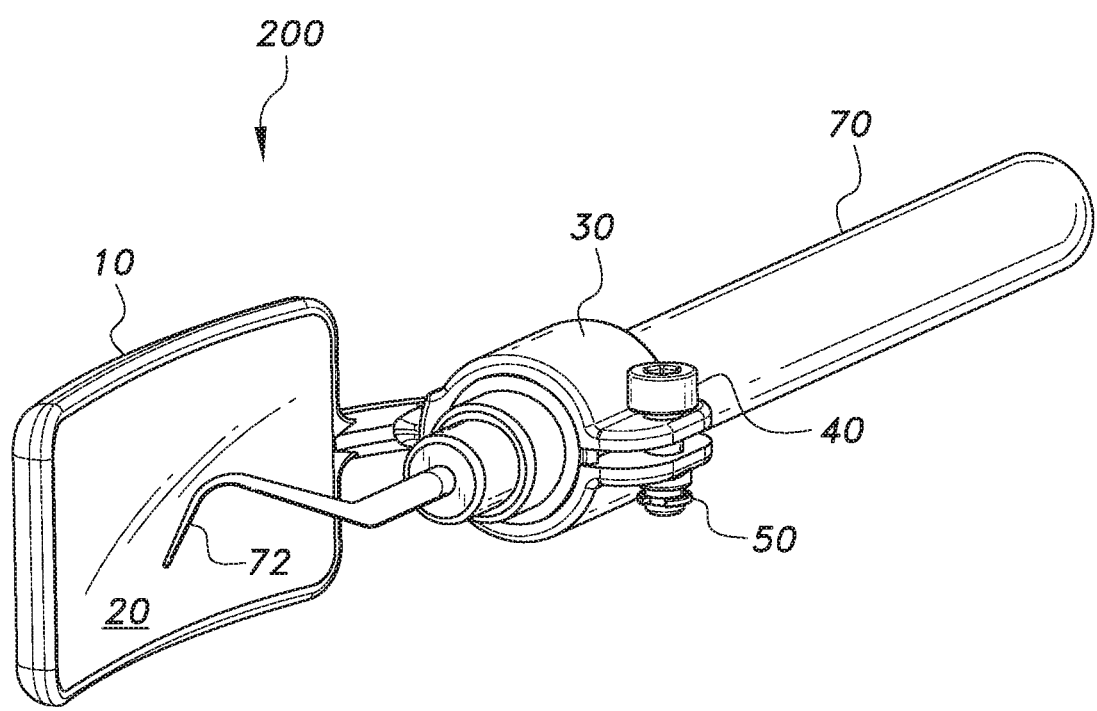
FIG. 6 is an environmental, perspective view of a combination cheek retractor/mouth mirror attachment for a dental tool, shown attached to a periodontal probe.

FIG. 4 is a top view of the attachment 100 and FIG. 5 is a section view, particularly showing the gaskets 36 protecting the handle of the explorer 60. Although FIGS. 1-5 show the attachment used in combination with a dental explorer 60, the attachment may be used in combination with other dental tools. FIG. 6 shows an embodiment of the attachment 200 used in combination with a periodontal probe 70. The attachment 200 has the same structure as the attachment 100, and will not be described further. The periodontal probe 70 is conventional, having an elongate handle and an angled probe head 72.

It is to be understood that the combination cheek retractor/mouth mirror attachment for a dental tool is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A combination cheek retractor/mouth mirror attachment in combination with a dental tool, comprising:
    a dental tool, the dental tool having an elongated handle portion, a neck portion and a probe head portion;
    a single unit combination cheek retractor/mouth mirror attachment to the dental tool, the combination cheek retractor/mouth mirror attachment consisting of:
        a cheek retractor, wherein the cheek retractor has an arcuate body of a predetermined length, the arcuate body having parallel upper and lower arcuate arms and parallel vertical legs joining opposite ends of the upper and lower arms to define an outer curved rectangular frame;
        a mouth mirror fixed to the cheek retractor, wherein the mouth mirror is an arcuate, single-faced plane mirror affixed to the cheek retractor within the outer curved rectangular frame;
        a split ring collar extending from the cheek retractor, wherein the splint ring collar has parallel tabs extending normal to the split ring collar, the parallel tabs having aligned holes defined therein and a fastener selectively disposed through the aligned holes in the parallel tabs, the split ring collar further including a snap ring removably attached to the fastener to secure the splint ring collar to the neck portion of the dental tool; and
        an arcuate connector arm, the arcuate connector arm being configured and angled to follow the arcuate contour of the arcuate body of the cheek retractor and being dimensioned to have a length less than the predetermined length of the arcuate body of the cheek retractor, wherein the arcuate connector arm is disposed between the cheek retractor and the split ring collar,
    whereby the cheek retractor permits the cheeks to spread in such a manner as to ensure free access to the areas to be treated and reduce any pain and discomfort to the patient.

2. The combination cheek retractor/mouth mirror attachment in combination with a dental tool according to claim 1, wherein the probe head portion comprises a dental explorer.

3. The combination cheek retractor/mouth mirror attachment in combination with a dental tool according to claim 1, wherein the probe head portion comprises a periodontal probe.

4. The combination cheek retractor/mouth mirror attachment in combination with a dental tool according to claim 1, wherein the arcuate arm is disposed at a fixed angle of 40° with respect to the plane of the top edge of the split ring collar and the arcuate body of the cheek retractor.

* * * * *